United States Patent
Kakimoto et al.

(10) Patent No.: US 10,604,779 B2
(45) Date of Patent: Mar. 31, 2020

(54) METHOD FOR PRODUCTION OF MUTANT-TYPE HUMAN ERYTHROPOIETIN

(71) Applicant: JCR Pharmaceuticals Co., Ltd., Ashiya-shi, Hyogo (JP)

(72) Inventors: Shinji Kakimoto, Kobe (JP); Miroslav Matev, Kobe (JP); Tsuyoshi Fukui, Kobe (JP); Yukichi Hatano, Kobe (JP); Junya Tani, Kobe (JP); Kazutoshi Mihara, Kobe (JP); Kenichi Takahashi, Kobe (JP); Atsushi Sugimura, Kobe (JP)

(73) Assignee: JCR PHARMACEUTICALS CO., LTD., Hyogo (JP)

( * ) Notice: Subject to any disclaimer, the term of this patent is extended or adjusted under 35 U.S.C. 154(b) by 0 days.

(21) Appl. No.: 16/083,408

(22) PCT Filed: Mar. 7, 2017

(86) PCT No.: PCT/JP2017/008907
§ 371 (c)(1),
(2) Date: Sep. 7, 2018

(87) PCT Pub. No.: WO2017/154869
PCT Pub. Date: Sep. 14, 2017

(65) Prior Publication Data
US 2019/0078129 A1    Mar. 14, 2019

(30) Foreign Application Priority Data

Mar. 9, 2016 (JP) ................. 2016-045338

(51) Int. Cl.
| | | |
|---|---|---|
| C12P 21/02 | (2006.01) | |
| C07K 1/16 | (2006.01) | |
| C12N 15/09 | (2006.01) | |
| C12N 15/52 | (2006.01) | |

(52) U.S. Cl.
CPC ............. *C12P 21/02* (2013.01); *C07K 1/16* (2013.01); *C12N 15/09* (2013.01); *C12N 15/52* (2013.01)

(58) Field of Classification Search
None
See application file for complete search history.

(56) References Cited

U.S. PATENT DOCUMENTS

| | | | |
|---|---|---|---|
| 7,619,073 B2 | 11/2009 | Schumann et al. | |
| 8,796,206 B2 * | 8/2014 | Sloey | A61K 9/0019 514/7.7 |
| 2008/0207487 A1 * | 8/2008 | DeFrees | C07K 1/165 514/1.1 |

FOREIGN PATENT DOCUMENTS

| | | |
|---|---|---|
| EP | 2727930 | 5/2014 |
| JP | H08506023 A | 7/1996 |
| JP | 2002529475 A | 9/2002 |
| JP | 2009502117 A | 1/2009 |
| JP | 2011521993 A | 7/2011 |
| JP | 2011525492 A | 9/2011 |
| JP | 2013505276 A | 2/2013 |
| JP | 2014532080 A | 12/2014 |
| WO | 2010/008823 | 1/2010 |
| WO | 2011024024 A | 3/2011 |
| WO | 2011063195 A2 | 5/2011 |
| WO | 2011/156369 | 12/2011 |
| WO | 2013002330 A1 | 1/2013 |
| WO | 2014204023 A1 | 12/2014 |
| WO | 2015080509 A1 | 6/2015 |

OTHER PUBLICATIONS

International Search Report and Written Opinion issued in PCT/JP2017/008907, dated Apr. 18, 2017, 10 pages.

* cited by examiner

*Primary Examiner* — Karlheinz R. Skowronek
*Assistant Examiner* — Ronald T Niebauer
(74) *Attorney, Agent, or Firm* — Hamre, Schumann, Mueller & Larson, P.C.

(57) ABSTRACT

Disclosed is a highly efficient method for production of highly pure mutant-type human erythropoietin. The method is for production of mutant-type human erythropoietin, in which a transformed mammalian cell is allowed to produce the mutant-type human erythropoietin, and the supernatant of the culture is subjected to hydrophobic column chromatography, multimodal anion exchange column chromatography, anion exchange column chromatography, phosphate group affinity column chromatography, and gel filtration column chromatography, in this order.

7 Claims, 1 Drawing Sheet
Specification includes a Sequence Listing.

SEQUENCE LISTING

```
<160> NUMBER OF SEQ ID NOS: 3

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Lys Arg Ser Lys Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Met Phe Leu Arg Gly Lys Leu Lys Leu Tyr Thr Gly Glu Ala
145                 150                 155                 160
```

Cys Arg Thr Gly Asp
            165

<210> SEQ ID NO 2
<211> LENGTH: 165
<212> TYPE: PRT
<213> ORGANISM: Artificial Sequence
<220> FEATURE:
<223> OTHER INFORMATION: Darbepoetin

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Asn Glu Thr
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Val Asn Glu Thr Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
            165

<210> SEQ ID NO 3
<211> LENGTH: 721
<212> TYPE: DNA
<213> ORGANISM: Artificial Sequence
<220> FEATURE:
<223> OTHER INFORMATION: Synthetic DNA containing darbepoetin-coding
      region

<400> SEQUENCE: 3
ccgacgcgtc gccaccatgg gggtgcacga gtgtcctgcc tggctgtggc ttctcctgtc     60
cctgctgtcg ctccctctgg gcctcccagt cctgggcgcc ccaccacgcc tcatctgtga    120
cagccgagtc ctggagaggt acctcttgga ggccaaggag gccgagaata tcacgacggg    180
ctgtaacgaa acctgcagct tgaatgagaa tatcactgtc ccagacacca agttaatttt    240
ctatgcctgg aagaggatgg aggtcgggca gcaggccgta gaagtctggc agggcctggc    300
cctgctgtcg gaagctgtcc tgcggggcca ggccctgttg gtcaactctt cccaggtgaa    360
cgagaccctg cagctgcatg tggataaagc cgtcagtggc cttcgcagcc tcaccactct    420
gcttcgggct ctgggagccc agaaggaagc catctcccct ccagatgcgg cctcagctgc    480
tccactccga acaatcactg ctgacacttt ccgcaaactc ttccgagtct actccaattt    540
cctccgggga agctgaagc tgtacacagg ggaggcctgc aggacagggg acaggtgact    600
acccaggagt ccctggctgc caggagagtt gggcctgagt tcccctctt ggacccagag    660

```
agcttgtgac gcctcctccc tgctgctaat aaaactactc agcttctaag cggccgccaa    720
a                                                                   721
```

METHOD FOR PRODUCTION OF MUTANT-TYPE HUMAN ERYTHROPOIETIN

TECHNICAL FIELD

The present invention relates to a method for production of mutant-type human erythropoietin, in particular to a method for production of mutant-type human erythropoietin by letting transformant mammalian cells produce mutant-type human erythropoietin, obtaining the culture supernatant, and subjecting this to a purification method in which multiple specific chromatography steps are carried out in a specific order.

BACKGROUND ART

Human erythropoietin (hEPO) is a glycoprotein which boosts production of erythrocytes by acting on erythroid progenitors to promote their differentiation into erythrocytes in human. For this reason, hEPO has been used as a medicament for the treatment of human renal anemia, as well as in preserving autologous blood in preparation for an operation. Erythropoietin is a glycoprotein consisting of 165 amino acid residues, in which the asparagine residues at positions 24, 38, and 83 from its N-terminus are modified with N-linked sugar chains, and the serine residue at position 126 with an O-linked sugar chain, respectively. Thus, the peptide chain of hEPO is modified with sugar chains at four positions. These sugar chains contribute to the stability of hEPO in the body, and hEPO stripped of those sugar chains shows little activity because it is rapidly decomposed in the body.

Aiming to increase the stability of hEPO in the body, various attempts have been made to build mutant-type hEPOs having altered amino acid sequence so as to be modified by an increased number of sugar chains. Darbepoetin is one of such mutant-type hEPOs. Darbepoetin is a mutant-type hEPO which has mutations introduced at five positions in its peptide chain consisting of 165 amino acid residues: Ala30Asn, His32Thr, Pro87Val, Trp88Asn, and Pro90Thr (Patent Document 1). Among these mutations, asparagine residues at two positions, Ala30Asn and Trp88Asn, provide fresh sites for binding of N-linked sugar chains. Since wild-type hEPO possesses four sites for binding of sugar chains as mentioned above, darbepoetin consequently has six sites in total for binding of sugar chains. Actually, darbepoetin produced using CHO cells, which originate from Chinese hamster ovary, is modified at those six positions with sugar chains. Such a form of darbepoetin was approved as an ethical drug in the name of Nesp (registered trademark) in 2010 in Japan.

The generally recommended dosage of Nesp is weekly 20 µg i.v. as the starting dose, then biweekly 30-120 µg i.v. as the maintenance dose for a patient receiving hemodialysis; and for a patient receiving peritoneal dialysis or a predialysis patient with chronical renal failure, biweekly 30 µg s.c. or i.v. as the starting dose, then 60-180 µg s.c. or i.v. every four weeks as the maintenance dose. Compared with other erythropoietin preparations which generally require administration two or three times a week, Nesp lessens patient's burden by reducing administration frequency.

As a method for production of mutant type erythropoietin using CHO cells, a method is reported, in which a mutant erythropoietin expressed by culturing transformed CHO cells in a serum-free medium is purified by a four-step chromatography using a mixed mode column (Capto Adhere column), a first cation exchange column, a second cation exchange column, and anion exchange column (or Capto Adhere column)(Patent Documents 2-3). The method in this report is aimed to isolate an isoform of mutant erythropoietin having a low isoelectric point, and characterized in that the mutant erythropoietin is first adsorbed by the resin in the mixed mode column process and the resin then is washed in an acidic condition (pH 4.0).

Further, as for a method for production of a mutant type erythropoietin using transformed CHO cells, there is reported a method, in which the mutant erythropoietin expressed by culturing such CHO cells is purified by a three-step chromatography using an affinity column based on lectin/m-aminophenyl matrix, an anion exchange column, and a hydrophobic column (Patent Document 4). Furthermore, a method for purification of a mutant-type erythropoietin expressed by culturing transformed CHO cells in a serum-free medium is reported, which method employs a hydrophobic column, an anion exchange column, a weak cation exchange column, and a strong cation exchange column (Patent Document 5). Furthermore, a method for purification is reported in which a mutant-type erythropoietin expressed by transformed CHO cells in a serum-free medium is purified through a three-step chromatography employing a first anion exchange column, a hydroxyapatite column, and a second anion exchange column (Patent Document 6). Still further, there are reported a method in which a mutant-type erythropoietin expressed by culturing transformed CHO cells is purified through a three-step chromatography using a dye-affinity column, a hydroxyapatite column, and an anion exchange column (Patent Document 7), and a method for purification of mutant-type human erythropoietin which includes a step of washing an anion exchange column in which the mutant-type erythropoietin is adsorbed with an arginine-containing buffer (Patent Document 8).

PRIOR ART DOCUMENTS

Patent Documents

[Patent Document 1] JPH08-506023
[Patent Document 2] JP2011-525492
[Patent Document 3] WO2011-063195
[Patent Document 4] JP2009-502117
[Patent Document 5] WO2011/024024
[Patent Document 6] JP2014-532080
[Patent Document 7] WO2014/204023
[Patent Document 8] WO2015/080509

SUMMARY OF INVENTION

Technical Problem

It is an objective of the present invention to provide a method to efficiently purify a mutant-type human erythropoietin from a culture of the mutant-type human erythropoietin-producing cells, to such a high purity as allows it to be used as a medicament for the treatment of, e.g., renal anemia.

Solution to Problem

In the study for the above purpose, the present inventors found that a mutant-type human erythropoietin contained in the culture supernatant of a mutant-type human erythropoietin-producing cells cultured in a serum-free medium, can be efficiently purified to a high purity by applying it to hydrophobic column chromatography, multimodal anion exchange column chromatography, anion exchange column chromatography, column chromatography employing a solid phase having affinity to phosphate groups, and gel filtration column chromatography, in this order. The present invention was completed through further studies conducted based on these findings. Thus, the present invention provides what follows.

1. A method for production of a mutant-type human erythropoietin comprising the amino acid sequence set forth as SEQ ID NO:2, the method comprising;

(a) a step of providing a mutant-type human erythropoietin-producing mammalian cell which produces the mutant-type human erythropoietin, (b) a step of culturing the mutant-type human erythropoietin-producing mammalian cell in a serum-free medium to let the cell secrete the mutant-type human erythropoietin into the culture, (c) a step of preparing a supernatant by removing the cell from the culture, (d) a step of subjecting the supernatant to hydrophobic column chromatography to collect a fraction containing the mutant-type human erythropoietin, (e) a step of subjecting the fraction collected in the directly preceding step to multimodal anion exchange column chromatography to collect a fraction containing the mutant-type human erythropoietin, (f) a step of subjecting the fraction collected in the directly preceding step to anion exchange column chromatography to collect a fraction containing the mutant-type human erythropoietin, (g) a step of subjecting the fraction collected in the directly preceding step to column chromatography that employs a solid-phase material having affinity to phosphate group to collect a fraction containing the mutant-type human erythropoietin, and (h) a step of subjecting the fraction collected in the directly preceding step to gel filtration column chromatography to collect a fraction containing the mutant-type human erythropoietin, in this order.

2. The method for production according to 1 above, wherein a hydrophobic resin employed in the hydrophobic column chromatography has a phenyl group, wherein an ion exchanger employed in the multimodal anion exchange column chromatography is a strong anion exchanger having selectivity based on hydrophobic interaction and hydrogen bonding, and wherein the solid-phase material having affinity to phosphate group is hydroxyapatite or fluoroapatite.

3. The method for production according to 1 or 2 above, wherein the solid-phase material having affinity to phosphate group is hydroxyapatite.

4. The method for production according to one of 1-3 above, wherein the ion exchanger employed in the multimodal anion exchange column chromatography has an N-benzyl-N-methylethanolamine group as the functional group.

5. The method for production according to one of 1-4 above, wherein the ion exchanger employed in the anion exchange column chromatography has a diethylaminoethyl group as the functional group.

6. The method for production according to one of 1-5 above, further comprising a step of subjecting the fraction collected in step (h) above to a virus elimination treatment or a virus inactivation treatment.

Effects of Invention

The present invention enables purification of a mutant-type human erythropoietin to a high purity that allows it to be used as a therapeutic drug for renal anemia, efficiently from a culture of mutant-type human erythropoietin-producing cells.

DESCRIPTION OF EMBODIMENTS

Figure 1:
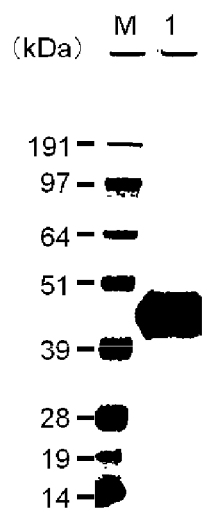
FIG. 1 shows the result of SDS-PAGE electrophoresis, where lane l and lane M show the migration patterns of purified darbepoetin and molecular weight markers, respectively.

In the present invention, the term "human erythropoietin" or "hEPO" means the glycoprotein having a peptide chain consisting of 165 amino acid residues set forth as SEQ ID NO:1. Naturally occurring human erythropoietin is modified with N-linked sugar chains on its asparagine residues located at positions 24, 38, and 83 from the N-terminus, and with O-linked sugar chains on the serine residue located at position 126 from the N-terminus. A recombinant human erythropoietin (rhEPO) expressed in CHO cells is also modified with sugar chains on these four amino acid residues. Those sugar chains contribute to stabilization of hEPO in the body, and hEPO stripped of its sugar chains shows little activity in vivo, because it is rapidly decomposed in the body.

In the present invention, the term "mutant-type human erythropoietin" or "mutant-type hEPO" means a glycoprotein in which substitution, deletion, insertion, or addition takes place at one or more of the amino acid residues forming the hEPO peptide chain so that at least one amino acid residue newly emerges that provides a fresh site for sugar chain binding. In this regard, such an amino acid residue that provides a fresh site for sugar chain binding is an asparagine residue, which can be modified with an N-linked sugar chain, or a serine or threonine residue, which can be modified with an O-linked sugar chain. More specifically, in order to create a fresh site for sugar chain binding by substitution of amino acid residue, an amino acid residue to be substituted is chosen from those located at positions 30, 68, 69, 71, 88, 125, and 127 of the 165 amino acid residues forming human erythropoietin set forth as SEQ ID NO:1, and one or more of them are replaced with asparagine, threonine, or serine residue. When replacing an amino acid residue with asparagine, one or two adjacent amino acid residues on the C-terminus side to that amino acid residue to be replaced with asparagine, if needed, are also replaced so that an amino acid sequence, Asn-X-Ser or Asn-X-Thr (X denotes an amino acid residue except proline), will occur in the amino acid sequence after the replacement.

A preferable embodiment of mutant-type human erythropoietin is darbepoetin, which corresponds to the amino acid sequence formed by introducing mutations into the 165 amino acids forming hEPO at five positions, Ala30Asn, His32Thr, Pro87Val, Trp88Asn, and Pro90Thr, thus having a peptide chain consisting of the 165 amino acid sequence set forth as SEQ ID NO:2. Among these mutations, the asparagine residues at two positions, Ala30Asn and Trp88Asn, are the binding sites for N-linked sugar chains. As wild-type hEPO has four binding sites for sugar chains, darbepoetin thus has six binding sites for sugar chains.

In the present invention, a mutant-type human erythropoietin can be produced by introducing a DNA fragment encoding the mutant-type human erythropoietin into an expression vector, transforming cells (e.g., CHO cells) with the obtained vector into mutant-type human erythropoietin-producing cells (mutant-type hEPO producing cells), and culturing these cells in a medium. Thus, the mutant-type hEPO is accumulated in the medium as a glycoprotein which is modified with sugar chains on its amino acid residues at five or more positions, including one or more newly introduced positions for sugar chain binding.

An expression vector to be employed into which a DNA fragment encoding mutant-type human erythropoietin gene is incorporated for expression, may be any one of such vectors, without particular limitation, that express the gene when it is introduced into CHO cells. The gene incorporated in an expression vector may be placed downstream of a DNA sequence which can regulate transcription frequency of genes in mammalian cells (gene expression regulatory site). Examples of gene expression regulatory sites that can be used in the present invention include, for example, but not limited to, the cytomegalovirus-derived promoter, SV40 early promotor, and human elongation factor-1α (EF-1α) promotor, A preferable medium used for culturing mutant-type hEPO producing cells is a serum-free medium. The following medium is preferably used, for example: a medium containing amino acids 3-700 mg/L, vitamins 0.001-50 mg/L, monosaccharides 0.3-10 g/L, inorganic salts 0.1-10000 mg/L, trace elements 0.001-0.1 mg/L, nucleosides 0.1-50 mg/L, fatty acids 0.001-10 mg/L, biotin 0.01-1 mg/L, hydrocortisone 0.1-20 µg/L, insulin 0.1-20 mg/L, vitamin $B_{12}$ 0.1-10 mg/L, putrescine 0.01-1 mg/L, sodium pyruvate 10-500 mg/L, and water soluble ion compound. Where desired, thymidine, hypoxanthine, a conventional pH indicator, an antibiotic, and the like may be added to the medium.

A serum-free medium may be one which further contains one or more compounds selected from sodium bicarbonate, L-glutamine, D-glucose, insulin, selenous acid, diaminobutane, hydrocortisone, ferric sulfate, asparagine, aspartic acid, serine, and polyvinylalcohol. Furthermore, commercially available serum free mediums, such as CD OptiCHO (registered trademark) medium, CHO-S-SFM II medium, or CD CHO medium (Thermo Fisher Scientific Inc.), EX-CELL (registered trademark) 302 medium or EX-CELL (registered trademark) 325-PF medium (SAFC Biosciences Inc.) and the like, may be used as the basic medium, to which may be added compounds such as antibiotics as desired. For example, CD optiCHO™ medium, a serum free medium containing 16 µmol/L thymidine, 100 µmol/L hypoxanthine, and 2 mmol/L L-alanyl-L-glutamine may be used suitably for the culture of mutant-type hEPO producing cells.

By culturing mutant-type hEPO producing cells in a serum free medium, a mutant-type hEPO is accumulated in the medium. In the present invention, a mutant-type hEPO is purified starting from the supernatant collected after completion of the culture of mutant-type hEPO producing cells, through a purification process which includes a hydrophobic column chromatography step, a multimodal anion exchange column chromatography step, an anion exchange column chromatography step, a column chromatography step employing a solid phase material having affinity to phosphate group, and a gel filtration column chromatography step, in this order, to such purity levels as allow it to be used as a medicament.

The first step of the purification process, hydrophobic column chromatography, is a step to remove contaminants utilizing the hydrophobic interaction between the mutant-type hEPO or contaminants and the hydrophobic ligand attached to the hydrophobic resin. Though there is no specific restriction as to what kind of ligand is to be used in hydrophobic column chromatography, preferable is a ligand that has a phenyl group, and more preferable is a ligand that has a phenyl group linked to the resin body via a spacer arm such as R—O—CH$_2$—CH(OH)—CH$_2$—O—C$_6$H$_5$ (R denotes the resin body). An example of particularly preferred column materials is Phenyl Sepharose 6 Fast Flow (GE Healthcare Inc.), in which a phenyl group is covalently fixed via a certain spacer arm to the Phenyl Sepharose 6 Fast Flow matrix.

In the process of this hydrophobic column chromatography, before the culture supernatant is applied to the column, electrical conductivity of the culture supernatant is adjusted to not less than 15 S/m, e.g., 15-20 S/m, by addition of a neutral salt, and its pH is adjusted preferably to pH 7.0-8.0, more preferably to pH 7.3-7.7, and still more preferably to pH 7.5. And the hydrophobic resin of the hydrophobic column is equilibrated in advance preferably with 15-25 mM Tris buffer adjusted to pH 7.0-8.0 containing 1.5 M-2.5 M neutral salt, more preferably with 15-25 mM Tris buffer adjusted to pH 7.3-7.7 containing 1.8 M-2.2 M neutral salt, and still more preferably with 20 mM Tris buffer adjusted to pH 7.5 containing 2.0 M neutral salt. The neutral salt employed here is preferably NaCl or KCl, and more preferably NaCl. In this step, an active fraction not adsorbed by the column is collected (hydrophobic column chromatography-collected fraction). This collected fraction is subjected to the following step of purification, e.g., the second step of the purification process exemplified below. In the case where the collected fraction is applied to the second step of the purification process described below, e.g., the collected fraction which is desalinated in advance may be applied.

Multimodal anion exchange column chromatography, the second step of the purification process, is a step to remove contaminants using selectivity based on static electrical interaction, hydrophobic interaction, and hydrogen bonding between the mutant-type hEPO or contaminants and the multimodal anion exchanger resin. As a multimodal anion exchanger resin employed in the multimodal anion exchange column chromatography, a multimodal strong anion exchanger resin is preferred, and a particularly preferred column material is Capto adhere (GE Healthcare), which has an N-benzyl-N-methylethanolamine group as the functional group of the strong anion exchanger.

In the multimodal anion exchange column chromatography, the multimodal anion exchanger resin is equilibrated in advance preferably with 15-25 mM Tris buffer adjusted to pH 7.0-8.0, more preferably with 15-25 mM Tris buffer adjusted to pH 7.3-7.7, and still more preferably with 20 mM Tris buffer adjusted to pH 7.5. To this preequilibrated multimodal anion exchange resin is applied the fraction that has been collected from the hydrophobic column chromatography and then desalinated, to allow the mutant-type hEPO to be adsorbed by the resin.

The mutant-type hEPO adsorbed by the resin then is eluted preferably with 15-25 mM Tris buffer adjusted pH 7.3-7.7 containing 140-250 mM neutral salt, more preferably with 20 mM Tris buffer adjusted to pH 7.5 containing 140-250 mM neutral salt. The neural salt employed here is preferably NaCl or KCl, and more preferably NaCl. In this step, an active fraction being eluted is collected (multimodal anion exchange column chromatography-collected fraction).

The fraction thus collected is supplied to the next step of purification, e.g., the third step of the purification process exemplified below. In the case where the collected fraction is supplied to the third step of the purification process described below, it may, e.g., be diluted with purified water in advance.

Anion exchange column chromatography, the third step of the purification process, is a step utilizing selectivity based on static electrical interaction with the anion exchanger resin. As a resin employed in the anion exchange column chromatography, a weak anion exchange resin is preferred, and particularly preferred is the ion exchanger resin having a diethylamino group as the functional group.

In the anion exchange column chromatography, the anion exchanger resin is equilibrated in advance preferably with a 15-25 mM Tris buffer adjusted to pH 7.0-8.0, more preferably with a 15-25 mM Tris buffer adjusted to pH 7.3-7.7, and still more preferably with a 20 mM Tris buffer adjusted to pH 7.5. To this preequilibrated anion exchanger resin is applied a dilution of the fraction collected from the multimodal anion exchange column chromatography, to let the mutant-type hEPO be adsorbed by the resin.

The mutant-type hEPO adsorbed by the resin is eluted preferably with 15-25 mM Tris buffer adjusted to pH 7.3-7.7 containing 80-200 mM neutral salt, and more preferably with 20 mM Tris buffer adjusted to pH 7.5 containing 80-200 mM neutral salt. The neutral salt employed here is preferably NaCl or KCl, and more preferably NaCl. In this step, an active fraction eluted is collected (anion exchange column chromatography-collected fraction). This collected fraction then is subjected to the next step of purification, e.g., the fourth step of the purification process exemplified below.

Column chromatography using a solid phase material having affinity to phosphate group, the fourth step of the purification process, is a step to remove contaminants utilizing the solid phase materials having affinity to phosphate group. As a solid phase material employed here, preferred are hydroxyapatite or fluoroapatite, and particularly preferred is hydroxyapatite.

In the column chromatography using a solid phase material having affinity to phosphate group, the collected fraction from the preceding anion exchange column chromatography is adjusted in advance to lower than 0.3 S/m in its electrical conductivity, e.g., 0.1-0.29 S/m, and its pH is adjusted preferably to pH 6.8-7.2, and more preferably to pH 7.0. Further, the solid phase material is equilibrated in advance preferably with 40-60 mM MES buffer adjusted to pH 6.5-7.5 containing 1.8-2.2 mM calcium chloride and 1.8-2.2 mM sodium phosphate, and more preferably with 50 mM MES buffer adjusted to pH 7.0 containing 2 mM calcium chloride and 2 mM sodium phosphate. Onto this preequilibrated solid phase material is loaded the anion exchange column chromatography-collected fraction, which has been adjusted in its electrical conductivity and pH, to allow the mutant-type hEPO to be adsorbed by the solid phase material.

The mutant-type hEPO adsorbed by the solid phase material is eluted preferably with 40-60 mM MES buffer adjusted to pH 6.5-7.5 and containing 0.8-1.2 mM calcium chloride and 2.8-3.2 mM sodium phosphate, and more preferably with 50 mM MES buffer adjusted to pH 7.0 and containing 1 mM calcium chloride and 3 mM sodium phosphate. In this step, an active fraction is collected (phosphate group affinity column chromatography-collected fraction). This collected fraction is subjected to the next step of purification, e.g., the fifth step of the purification process described below.

Gel filtration column chromatography, the fifth step of the purification process, is a step to eliminate low molecular-weight contaminants such as endotoxin, and multimers or decomposition products of mutant-type hEPO. This step may be performed by a conventional method. Thus, by means of the purification process comprising the first to fifth steps mentioned above, the mutant-type hEPO is obtained that is purified to an extent that allows it to be used as a medicament.

A preferable example of the method for production according to the present invention is a method for production of a mutant-type human erythropoietin comprising the amino acid sequence set forth as SEQ ID NO:2, which method comprises; (a) a step of providing a mutant-type human erythropoietin-producing mammalian cell which produces the mutant-type human erythropoietin, (b) a step of culturing the mutant-type human erythropoietin-producing mammalian cell in a serum-free medium to let the cell secrete the mutant-type human erythropoietin into the culture, (c) a step of preparing a supernatant by removing the cell from the culture, (d) a purification step employing hydrophobic column chromatography, (e) a purification step employing multimodal anion exchange column chromatography, (f) a purification step using anion exchange column chromatography, (g) a purification using column chromatography that employs a solid-phase material having affinity to phosphate group, and (h) a purification step using gel filtration column chromatography, in this order.

In the above, one or more purification steps may be added before the first step of the purification process (before step (d)), between two adjacent steps of the first to the fifth purification steps (between steps (d) to (h)), or after the fifth purification step (step (h)). Examples of purification step that may be added include, but are not limited to, dye-affinity column chromatography, anion exchange column chromatography, cation exchange column chromatography, hydrophobic column chromatography, hydroxyapatite column chromatography, or fluoroapatite column chromatography.

A further preferable example of the method for production according to the present invention is a method for production of a mutant human erythropoietin comprising the amino acid sequence set forth as SEQ ID NO:2 comprising; (a) a step of providing a mutant-type human erythropoietin-producing mammalian cell which produces the mutant-type human erythropoietin, (b) a step of culturing the mutant-type human erythropoietin-producing mammalian cell in a serum-free medium to let the cell secrete the mutant-type human erythropoietin into the culture, (c) a step of preparing a culture supernatant by removing the cell from the culture, (d) a step of subjecting the culture supernatant to hydrophobic column chromatography to collect a fraction containing the mutant-type human erythropoietin, (e) a step of subjecting the fraction collected in the directly preceding step to multimodal anion exchange column chromatography to collect a fraction containing the mutant-type human erythropoietin, (f) a step of subjecting the fraction collected in the directly preceding step to anion exchange column chromatography to collect a fraction containing the mutant-type human erythropoietin, (g) a step of subjecting the fraction collected in the directly preceding step to column chromatography that employs a solid-phase material having affinity to phosphate group to collect a fraction containing the mutant-type human erythropoietin, and (h) a step of subjecting the fraction collected in the directly preceding step to gel filtration column chromatography to collect a fraction containing the mutant-type human erythropoietin, in this order.

In the above, one or more purification steps may be added before step (d) of the purification process, between any two adjacent steps of steps (d) to (h), or after step (h). Examples of purification steps that can be added include, but not limited to, dye-affinity column chromatography, anion exchange column chromatography, cation exchange column chromatography, hydrophobic column chromatography, hydroxyapatite column chromatography, or fluoroapatite column chromatography. In the case where an additional chromatography step is added between steps (d) and (e) above, for example, the term "the directly preceding step" in step (e) above indicates the additional step.

In the case where dye-affinity column chromatography is added as a step for purification, though there is no particular restriction as to what resin is to be employed for the dye-affinity column chromatography, blue triazine dye, in particular, can be used preferably, yet other triazine dyes are also suitable. A particularly preferred column is Blue Sepharose 6 Fast Flow (GE Healthcare), in which a dye Cibacron™ Blue F3GA is covalently fixed to the Sepharose 6 Fast Flow matrix.

A still further preferable example of the method for production according to the present invention is a method for production of a mutant-type human erythropoietin comprising the amino acid sequence set forth as SEQ ID NO:2, which method comprises (a) a step of providing a mutant-type human erythropoietin-producing mammalian cell which produces the mutant-type human erythropoietin, (b) a step of culturing the mutant-type human erythropoietin-producing mammalian cell in a serum-free medium to let the cell secrete the mutant-type human erythropoietin into the culture, (c) a step of preparing a supernatant by removing the cell from the culture, (d) a step of subjecting the supernatant to hydrophobic column chromatography to collect a fraction containing the mutant-type human erythropoietin, (e) a step of subjecting the fraction collected in step (d) above to multimodal anion exchange column chromatography to collect a fraction containing the mutant-type human erythropoietin, (f) a step of subjecting the fraction collected in step (e) above to anion exchange column chromatography to collect a faction containing the mutant-type human erythropoietin, (g) a step subjecting the fraction collected in step (f) above to column chromatography that employs a solid-phase material having affinity to phosphate group to collect a fraction containing the mutant-type human erythropoietin, and (h) a step of subjecting the fraction collected in step (g) above to gel filtration column chromatography to collect a fraction containing the mutant-type human erythropoietin, in this order.

A step for virus inactivation treatment or virus elimination treatment may be added as desired to the purification process according to the present invention. Though there is no particular restriction as to what kind of virus inactivation or virus elimination method is to be applied, solvent-detergent method or nanofiltration method, respectively, is preferred. Such an additional step for virus inactivation or virus elimination may be introduced into any two adjacent steps of the purification process, and it may even be positioned after completion of the last step of the purification process so long as that would not affect the composition of drug substance. Preferably, nanofiltration method is conducted after completion of the last step of the above purification process.

EXAMPLES

Though the present invention is described in further detail below with reference to examples, it is not intended that the present invention be limited by the examples.

(Construction of Darbepoetin Expression Vector)

A DNA fragment set forth as SEQ ID NO:3 was chemically synthesized which included a nucleotide sequence in which WAP-3' UTR (3' untranslated region of whey acidic protein) was placed on the 3' side of a nucleotide sequence encoding darbepoetin. In SEQ ID NO:3, 4-9 bp from the 5' end is a MluI recognition sequence, 98-592 bp a nucleotide sequence corresponding to the darbepoetin amino acid sequence, 599-709 bp a sequence of WAP-3' UTR, and 710-717 bp a NotI recognition sequence. This DNA fragment was digested with MluI and NotI, and inserted between MluI and NotI of pE-neo vector to produce pE-neo(DEPO), which was used as the darbepoetin expression vector. Besides, pE-neo vector had been constructed in accordance with a method described in WO2013/161958.

(Establishment of Darbepoetin-expressing Cells)

CHO (CHO—K1) cells were purchased from ATCC. The CHO cells were transformed with pE-neo(DEPO) vector by electroporation using a Gene Pulser Xcell™ electroporation system (BioRad Inc.). The transformed cells were selection cultured in a selection medium, and a darbepoetin expressing cell line was obtained by the limiting dilution method. As the selection medium employed here was CD optiCHO™ medium (Life Science Inc.), a serum-free medium containing 1×HT Supplement, 10 mg/L recombinant human insulin, 4 mM GlutaMax™ (Thermo Fisher Inc.), and 0.78 mg/mL G418. The cell line thus obtained was cryopreserved in liquid nitrogen until use for producing darbepoetin.

(Preculture of Darbepoetin-expressing Cells)

The above cryopreserved cells were thawed in a 37° C. water bath, and suspended in CD optiCHO™ medium, a serum-free medium containing 16 µM thymidine, 100 µM hypoxanthine, 10 mg/L recombinant human insulin, 4 mM L-alanyl-L-glutamine, and 0.8 g/L G-418 (preculture medium), and then were settled by centrifugation to remove the supernatant. The settled cells were suspended at a density of $2 \times 10^5$ cells/mL in the preculture medium, and cultured for 3-4 days at 37° C. in the presence of 5% $CO_2$. Culture was repeated in this manner until the number of the cells grew at least to $4 \times 10^{11}$ while expanding the scale of culture.

(Production Culture of Darbepoetin-expressing Cells)

The cells grown in the preculture were suspended at a density of $2 \times 10^5$ cells/mL in 2000 L of CD optiCHO™ medium, a serum-free medium containing 16 µM thymidine, 100 µM hypoxanthine, and 2 mM L-alanyl-L-glutamine (medium for production culture), and cultured in jar fermenter for 8 days at 37° C. stirring at 60 rpm.

(Purification of Darbepoetin (Hydrophobic Column Chromatography Step))

Following the production culture, the culture was filtered, using first Millistak+ (registered trademark) HC pod filter grade DOHC (1.1m²×18, Merck Inc.), and then Millistak+ HC pod filter grade A1HC (1.1 m²×8, Merck Inc.) to remove cells, and were further filtered through Durapore Opticap XLT20 (pore size: 0.22 µm, Merck Inc.) to obtain the culture supernatant. The culture supernatant then was concentrated to one-tenth of its volume using a ultrafiltration membrane, Pellicon 3 Cassette w/Ultracel PLCTK Membrane, 30 kDa (Merck Inc.). During this concentration process, the electrical conductivity of the solution was maintained at 50 S/m or over by addition of 0.1 M Tris-HCl buffer (pH 7.5) containing 5 M NaCl. To the solution thus concentrated (concentrated solution) was added 1 M Tris-HCl. buffer (pH 8.8) to adjust its pH and conductivity to pH 7.5 and 15 S/m or over, respectively.

This concentrated and pH adjusted solution was applied at a linear flow rate of 100 cm/hr onto a hydrophobic column, Phenyl Sepharose 6 Fast Flow (high sub) (column volume: approx. 19.2 L, bed height: 20 cm, GE Healthcare Inc.), which had been equilibrated with three column volumes of 20 mM Tris-HCl buffer (pH 7.5) containing 2 M NaCl. The unabsorbed fraction flowing out of the column was collected. Consecutively, two column volumes of 20 mM Tris-HCl buffer (pH 7.5) containing 2 M NaCl was supplied to the column at the same flow rate to wash the column. The washing solution flowing out of the column was collected. The collected unabsorbed fraction and the washing solution were combined into one fraction, which was supplied to the next step of purification.

(Purification of Darbepoetin (Multimodal Anion Column Chromatography Step))

The fraction collected in the hydrophobic column chromatography step was concentrated using a ultrafiltration membrane, Pellicon 3 Cassette w/Ultracel PLCTK Membrane (molecular weight cut-off: 30 kDa, Merck Inc.) while adding 20 mM Tris-HCl (pH 7.5) buffer.

The concentrated solution was loaded onto a multimodal anion exchange column chromatography, Capto adhere (column volume: approx. 19.2 L, bed height: 20 cm, GE Healthcare Inc.), which had been equilibrated with three column volumes of 20 mM Tris-HCl (pH 7.5) buffer, at a linear flow rate of 150 cm/hr. Consecutively, two column volumes of 20 mM Tris-HCl buffer (pH 7.5) were supplied at the same flow rate to wash the column. The column then was supplied with 3.5 column volumes of 20 mM Tris-HCl buffer (pH 7.5) containing 140-250 mM NaCl, at the same flow rate, and the fraction thus collected was supplied to the next step of purification.

(Purification of Darbepoetin (Anion Exchange Column Chromatography Step))

The fraction obtained in the multimodal anion exchange column chromatography step was diluted with purified water. The solution thus prepared was loaded onto anion exchange column chromatography, DEAE Sepharose Fast Flow (column volume: approx. 19.2 L, bed height: 20 cm, GE Healthcare Inc.), that had been equilibrated with three column volumes of 20 mM Tris-HCl buffer (pH 7.5), at a linear flow rate of 150 cm/hr. Consecutively, the column was supplied with ten column volumes of 20 mM Tris-HCl buffer (pH 7.5) at the same flow rate to wash the column. The column then was supplied with 4.5 column volumes of 20 mM Tris-HCl buffer (pH 7.5) containing 80-200 mM NaCl at the same flow rate, and the fraction thus obtained was subjected to the next step of purification.

(Purification of Darbepoetin (Hydroxyapatite Column Chromatography Step))

To the fraction obtained in the anion exchange column chromatography step was added 10 mM MES buffer (pH 7.0) to bring the electrical conductivity of the fraction below 0.3 S/m, and the pH of it then was adjusted to 7.0 with diluted hydrochloric acid.

This solution was loaded onto CHT Ceramic Hydroxyapatite Column Type I (column volume: approx. 19.2 L, bed height: 20 cm, BioRad Inc.), which had been equilibrated with four column volumes of 50 mM MES buffer (pH 7.0) containing 2 mM $CaCl_2$ and 2 mM sodium phosphate, at a linear flow rate of 300 cm/hr. Consecutively, three column volumes of 50 mM MES buffer (pH 7.0) containing 2 mM $CaCl_2$ and 2 mM sodium phosphate was applied at the same flow rate to wash the column. The column then was supplied with 7.5 column volumes of 50 mM MES buffer (pH 7.0) containing 1 mM $CaCl_2$ and 3 mM sodium phosphate at the same flow rate, and the fraction thus obtained was subjected to the next step of purification.

(Purification of Darbepoetin (Gel Filtration Column Chromatography Step))

The fraction obtained in the hydroxyapatite column chromatography step was concentrated using an ultrafiltration membrane, Pellicon 3 Cassette w/Ultracel PLCTK membrane (molecular weight cut-off: 10 kDa, Merck Inc.).

This concentrated solution was loaded onto a gel filtration column, Superdex 200 prep grade column (column volume: approx. 38.5 L, bed height: 40 cm, GE Healthcare Inc.), which had been equilibrated with 1.5 column volumes of 20 mM phosphate buffer (pH 6.2) containing 137 mM NaCl, at a linear flow rate of 25 cm/hr. The same buffer was continuously supplied at the same flow rate, and the fraction that showed absorbance at 280 nm was collected as the fraction containing purified darbepoetin.

(Determination of Darbepoetin at Each Purification Step)

The amount of darbepoetin after each of the above purification steps was determined by EILSA as described below. As Table 1 shows, 45.3 g darbepoetin was applied to the first step of the purification process, i.e., hydrophobic column chromatography, and 10.28 g purified darbepoetin was finally recovered. Thus, the recovery rate of darbepoetin through the above purification method was found to be 23%, which indicated that the above purification method was a highly efficient way of purifying darbepoetin. Besides, in Table 1, "Recovery ratio/Step" denotes the ratio of the amount of darbepoetin recovered to the amount of darbepoetin applied within each step, and "Recovery ratio/Whole" denotes the ratio of the amount of darbepoetin recovered in each step to the initial amount of darbepoetin subjected to the purification process.

TABLE 1

Recovery ratio of darbepoetin at each step of purification

| Purification process | Darbepoetin | | | |
|---|---|---|---|---|
| | Amount loaded (g) | Amount recovered (g) | Recovery rate/Step (%) | Recovery rate/Whole (%) |
| Hydrophobic column | 45.30 | 46.98 | 104 | 104 |
| Multimodal anion exchange column | 46.98 | 33.98 | 72 | 75 |
| Weak anion exchange column | 33.98 | 12.08 | 36 | 27 |
| Hydroxyapatite column | 12.08 | 9.74 | 81 | 22 |
| Gel filtration column | 9.74 | 10.28 | 106 | 23 |

(Determination Method of Darbepoetin by ELISA)

Mouse anti-hEPO antibody was diluted to 2.5 μg/mL with Coating solution (Kirkegaard & Perry Laboratories Inc.), and 100 μL of this diluted antibody solution was added to each well of a 96-well plate (Thermo Scientific Inc.). The plate was left undisturbed for 12 hours at 4° C., or for 1 hour at room temperature, to immobilize the antibody to the plate. Following removal of the solution, 300 μL of PBS-T solution (0.01 M sodium phosphate, 0.138 M NaCl, 0.0027 M KCl, 0.05% Tween20, pH 7.4) containing 1% BSA was added to each well, and the plate was left undisturbed for 30 minutes at room temperature for blocking. After discarding the solution, each well was washed three times with PBS-T solution, to which then was added 80 μL of the sample that had been diluted to a suitable concentration, and the plate was shaken for 1 hour at room temperature on a plate mixer. In parallel, to each well was added a standard solution, which had been prepared by diluting the purified darbepoetin produced according to the present invention, quantified by amino acid analysis, and diluted to a concentration of 0.5-100 ng/mL.

The solution was discarded, and after washing each well three times with PBS-T solution, 80 μL of biotin-labelled mouse anti-hEPO monoclonal antibody was added to each well as the secondary antibody. Consecutively, 80 μL of NeutrAvidin-HRP solution was added to each well, and the plate was shaken on a plate mixer for one hour at room temperature. After washing each well three times with PBS-T solution, TMB substrate solution (Kirkegaard & Perry Laboratories Inc.) was added, and the plate was left undisturbed for 4-8 minutes at room temperature, and then 100 μL of TMB Stop Solution (Kirkegaard & Perry Laboratories inc.) was added to terminate the reaction. Absorbance at 450 nm was measured on a microwell plate reader. A calibration curve was produced using measurements of standard solutions, and the measured value for each sample was interpolated into the calibration curve to determine the darbepoetin concentration in the sample.

(Purity Evaluation of Darbepoetin (SDS-PAGE Electrophoresis)

The darbepoetin purified through the above process was applied to SDS-PAGE electrophoresis under a reducing, heated condition (70° C., 10 min). Coomassie brilliant-blue staining of the gel revealed darbepoetin as a single band at the position of about 45 kDa of molecular weight (FIG. 1).

(Purity Evaluation of Darbepoetin (SE-HPLC Analysis)

Figure 2:
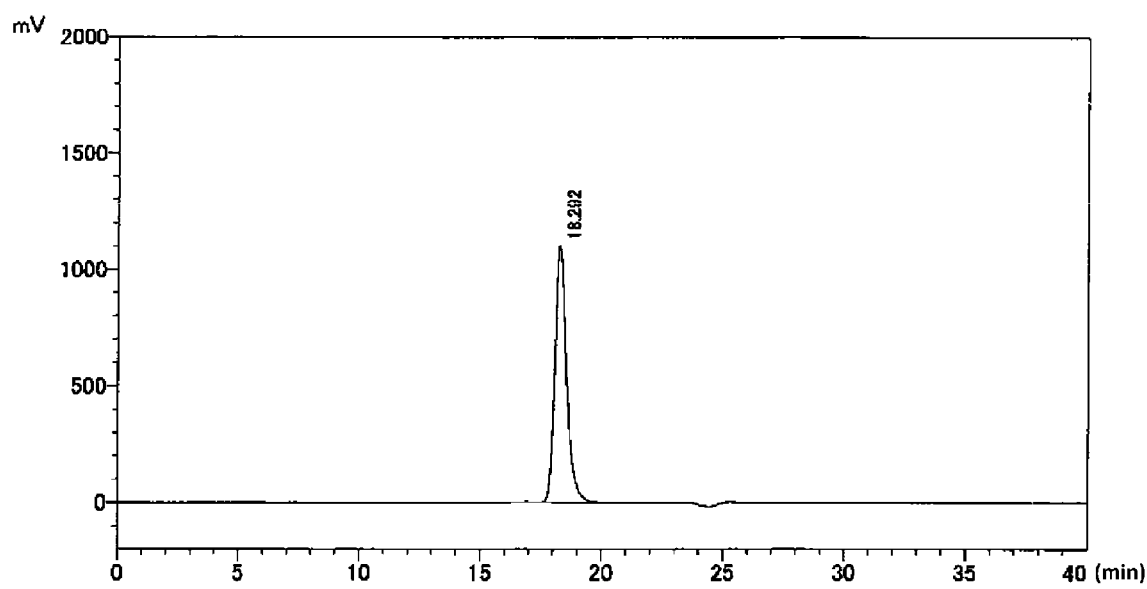
FIG. 2 shows the SE-HPLC chart produced with purified darbepoetin. The vertical and horizontal axes represent absorption at 215 nm and retention time (min), respectively.

SE-HPLC analysis was performed using an LC-20A system, SPD-20AV, UV/VIS detector (Shimadzu). TSKgel g3000SWXL column (7.8 mm I.D.×30 cm, TOSOH) was set in the LC-20A system, and after the column was equilibrated with phosphate buffer solution (200 mM sodium phosphate, 200 mM NaCl, pH 6.8) supplied at a linear flow rate of 0.5 mL/min, 100 μL of a solution containing darbepoetin purified above at the concentration of 0.2 mg/mL was loaded onto the column. While continuously supplying the PBS at the same flow rate, absorbance was monitored at 215 nm to produce an elution profile. In the elution profile produced in SE-HPLC analysis, the darbepoetin purified through the above process showed a single peak alone (FIG. 2).

The result of the above purity evaluation of darbepoetin indicates that darbepoetin purified by the above described purification process is substantially free of contaminants and with high purity that allows it to be directly used as a medicament for the treatment of such diseases as renal anemia.

INDUSTRIAL APPLICABILITY

The present invention enables provision of highly pure mutant-type human erythropoietin that can be used as a medicament for the treatment of such diseases as renal anemia.

SEQUENCE LISTING FREE TEXT

SEQ ID NO:2: darbepoetin
SEQ ID NO:3: synthetic DNA comprising the coding region for darbepoetin.

The invention claimed is:

1. A method for production of a mutant-type human erythropoietin comprising the amino acid sequence set forth as SEQ ID NO:2, the method comprising:
   (a) providing a mutant-type human erythropoietin-producing mammalian cell which produces the mutant-type human erythropoietin;
   (b) culturing the mutant-type human erythropoietin-producing mammalian cell in a serum-free medium to let the cell secrete the mutant-type human erythropoietin into a culture;
   (c) preparing a supernatant by removing the cell from the culture;
   (d) subjecting the supernatant to a hydrophobic column chromatography to collect a first fraction not adsorbed by the hydrophobic column and containing the mutant-type human erythropoietin;
   (e) subjecting the collected first fraction to a multimodal anion exchange column chromatography to collect a second fraction containing the mutant-type human erythropoietin;
   (f) subjecting the collected second fraction to an anion exchange column chromatography to collect a third fraction containing the mutant-type human erythropoietin;
   (g) subjecting the collected third fraction to a column chromatography that employs a solid-phase material having affinity to phosphate group to collect a fourth fraction containing the mutant-type human erythropoietin; and
   (h) subjecting the collected fourth fraction to a gel filtration column chromatography to collect a fifth fraction containing the mutant-type human erythropoietin, in this order.

2. The method for production according to claim 1, wherein a hydrophobic resin employed in the hydrophobic column chromatography has a phenyl group, wherein an ion exchanger employed in the multimodal anion exchange column chromatography is a strong anion exchanger having selectivity based on hydrophobic interaction and hydrogen bonding, and wherein the solid-phase material having affinity to phosphate group is hydroxyapatite or fluoroapatite.

3. The method for production according to claim 1, wherein the solid-phase material having affinity to phosphate group is hydroxyapatite.

4. The method for production according to claim 1, wherein an ion exchanger employed in the multimodal anion exchange column chromatography has an N-benzyl-N-methylethanolamine group as a functional group.

5. The method for production according to claim 1, wherein an ion exchanger employed in the anion exchange column chromatography has a diethylaminoethyl group as a functional group.

6. The method for production according to claim 1, further comprising a step of subjecting the collected fifth fraction to a virus elimination treatment or a virus inactivation treatment.

7. The method for production according to claim 1, wherein a hydrophobic resin employed in the hydrophobic column chromatography is equilibrated with 15-25 mM Tris buffer adjusted to pH 7.0-8.0 containing 1.5-2.5 M neutral salt.

* * * * *